(12) United States Patent
Wang et al.

(10) Patent No.: US 12,343,461 B2
(45) Date of Patent: Jul. 1, 2025

(54) DISINFECTING LIGHTING APPARATUS

(71) Applicant: LEDVANCE GmbH, Garching bei Munich (DE)

(72) Inventors: Yang Kevin Wang, Shenzhen (CN); Shengguo Yu, Shenzhen (CN)

(73) Assignee: LEDVANCE GMBH, Garching bei Munich (DE)

( * ) Notice: Subject to any disclaimer, the term of this patent is extended or adjusted under 35 U.S.C. 154(b) by 407 days.

(21) Appl. No.: 17/672,220

(22) Filed: Feb. 15, 2022

(65) Prior Publication Data

US 2022/0265891 A1 Aug. 25, 2022

(30) Foreign Application Priority Data

Feb. 25, 2021 (CN) .......................... 202110214477.X

(51) Int. Cl.
*A61L 9/20* (2006.01)
*A61L 9/18* (2006.01)

(52) U.S. Cl.
CPC ................. *A61L 9/205* (2013.01); *A61L 9/18* (2013.01); *A61L 2209/12* (2013.01); *A61L 2209/21* (2013.01)

(58) Field of Classification Search
None
See application file for complete search history.

(56) References Cited

U.S. PATENT DOCUMENTS

| | | | |
|---|---|---|---|
| 2002/0098109 A1* | 7/2002 | Nelson | A61L 2/10 422/123 |
| 2016/0207028 A1* | 7/2016 | Saleh | B01J 35/39 |
| 2020/0360912 A1* | 11/2020 | Seder | B01J 21/08 |
| 2021/0077653 A1* | 3/2021 | Maa | A61L 9/205 |
| 2021/0128774 A1* | 5/2021 | Maa | A61L 9/18 |
| 2021/0317981 A1* | 10/2021 | Higgins | F21V 3/00 |

FOREIGN PATENT DOCUMENTS

JP 2002150833 A * 5/2002

* cited by examiner

*Primary Examiner* — Andrew Smyth
(74) *Attorney, Agent, or Firm* — Hayes Soloway PC

(57) ABSTRACT

A luminaire is provided. The luminaire comprises a light source for generating a light, an electrical circuitry for driving the light source, and at least one air duct extending from an air inlet to an air outlet. The air ducts comprise walls with a photocatalytic element and are configured such that the air flowing through the at least one air duct can get in contact with the photocatalytic element and participate in a photocatalytic reaction under exposure to the light generated by the light source of the luminaire and/or an external light.

19 Claims, 13 Drawing Sheets

DISINFECTING LIGHTING APPARATUS

CROSS-REFERENCE TO RELATED APPLICATIONS

This patent application claims priority from Chinese Patent Application No. 202110214477.X, filed on Feb. 25, 2021, which is herein incorporated by reference in its entirety.

FIELD OF THE DISCLOSURE

The technical field of the present disclosure generally relates to lighting apparatuses. In particular, the present disclosure relates to a disinfecting lighting apparatus or luminaires.

BACKGROUND

Lighting apparatuses for providing light are known. Further, disinfection lighting apparatuses for providing ultra-violet (UV) radiation or UV sterilization lamps are known as well, in which the UV light directly or in combination with a UV photocatalyst is applied to kill germs. The UV radiation, however, is harmful to humans and animals, and therefore special measures must be taken to reduce the health risks related with the usage of such lamps. For instance, UV sterilization lamps are usually activated for a short time, in particular, in absence of people and after that are turned off again. Bacteria and viruses thus may recover when people come back. Further, in order to avoid a direct UV exposure of people, in some lighting apparatuses, UV lamps are placed inside a container, and special fans are provided for air circulation. These measures, however, cannot completely eliminate the risk of UV leakage and result in a complex design and high costs of disinfecting light apparatuses.

SUMMARY

An object of the present disclosure is to provide a particularly simple and safe disinfecting lighting apparatus.

According to the embodiments of the present disclosure, a luminaire is provided. The luminaire comprises a light source, in particular an LED light source, for providing a light, in particular, a visible light. In some embodiments, the light source may be configured for also providing a UV light. The luminaire further comprises an electrical circuitry, in particular, a driver, for driving the light source.

The luminaire also comprises at least one air duct extending from an air inlet or intake to an air outlet with air duct walls comprising a photocatalytic element or photocatalyst with a photocatalyst material. The at least one air duct is configured such that the air flowing through the at least one air duct can get in contact with the photocatalyst and participate in a photocatalytic reaction under exposure to the light generated by the light source of the luminaire and/or an external light.

The photocatalyst may, in particular, comprise a photocatalyst material or photocatalyst which produces reactive radicals under exposure to a visible light. In particular, the light may generate pairs of electrons and holes, and the photo-generated electrons may produce chemically active anion radicals like $O_2^-$ by reacting with $O_2$. The holes, on the other hand, may produce chemically active $\cdot OH$ radicals by reacting with water. Organic substances on its surface can be broken down by oxidation, eventually forming carbon dioxide and water. Thus, the luminaire can help in degradation of organic pollutants, sterilization, air purification, deodorization, and antifouling. Furthermore, because of the airflow in the duct, which can be propelled by the so-called chimney effect, in case of vertical ducts, the amount of the air which gets in contact with the photocatalyst over time can be increased such that the disinfection efficiency of the luminaire is increased.

The photocatalyst material may provide a practically limitless source of hydroxide radicals which can react with organic substances and destroy germs, bacteria, and fungus. With the growing consumer concern on organic pollutants, bacteria, and viruses, especially in view of the COVID-19 pandemic, the disinfection luminaire with a photocatalyst activatable with visible light can play a significant role in preventing or slowing down the spreading of infectious diseases.

In particular, the absorption spectrum of the photocatalyst material may be at wavelength between 380 nm and 780 nm. Thus, in contrast to conventional photocatalysts which can produce chemically active radicals under exposure to UV (ultra-violet) light, the photocatalytic element is activatable by visible light. In particular, the photocatalytic element of the luminaire may be activatable both by visible light and by UV light.

In case of LED light sources, the efficiency of the light generation in the UV spectral region may be lower than the efficiency of the light generation in the visible light spectrum. Thus, by using the photocatalytic element activatable by visual light, the overall efficiency of the luminaire can be increased.

The walls of the at least one air duct may comprise and/or be at least partially configured as an optical component for shaping the light generated by the light source, wherein the photocatalytic element is formed as a part of the optical component and/or is arranged on the optical component. The optical component may comprise, in particular, a lens, a diffuser, a reflector, or any combination thereof. The photocatalytic element may be, in particular, attached or applied to the optical component. Thus, the duct walls can combine both aerodynamic and optical function for improving both the optical performance, in particular, the light distribution, of the luminaire and the airflow for better air disinfection.

The walls of the at least one air duct may be configured as at least partially translucent diffusive optical components such that the light generated by the light source can pass across or through the walls of the at least one air duct to escape the luminaire. Thus, the ducts can serve both for air circulation for increased photocatalytic performance and for providing a pleasant diffuse light of the luminaire, while sharing the same general light source both for illumination and for catalyzation.

In some embodiments, the at least one air duct comprises at least two air ducts with an essentially equal bypass-ratio. By providing the essentially equal by-pass ratio of ducts, the air load of the ducts can be leveled such that the air drag in the air ducts can be minimized and the throughput of the air getting in touch with the photocatalyst can be increased. Thus, the photo-catalyzation performance can be improved while maintaining the small product size and the light output level without extensive light losses.

The luminaire may comprise a first housing or outer housing and a second housing or inner housing. The first housing and the second housing may be inserted or insertable into each other such that the at least one air duct is formed between the first housing and the second housing. By providing the first and second housings inserted into each other, the at least one air duct can be easily provided, and the costs for manufacturing the luminaire can be reduced.

In some embodiments, the first housing, the second housing, the light source, and/or the luminaire as a whole has an essentially axially symmetric shape, with the first housing, the second housing, and/or the light source being essentially coaxially arranged. Due to the axial symmetry of the luminaire, the design and manufacturing of the luminaire can be simplified, the air turbulences and the air drag in the ducts can be minimized, and an essentially symmetrical light distribution of the luminaire can be achieved.

The first housing and the second housing each may comprise a number of partitioning walls configured such that, when the first housing and the second housing are inserted into each other, the partitioning walls of the first housing and the partitioning walls of the second housing form a folded airway with a number of air ducts between the air inlet and the air outlet. Due to folded airways formed by the partitioning walls of the first housing and the second housing, the length of the air path within the luminaire can be easily multiplied, resulting in an increased disinfection performance of the luminaire.

The luminaire may comprise a fan for forcing the air through the at least one air duct of the luminaire. By forcing the air through the at least one duct, the throughput of the air getting in touch with the photocatalyst, and thus the photocatalytic efficiency of the luminaire, can be increased.

The photocatalytic element may comprise a film at least partially covering at least one wall of the at least one air duct. By providing the photocatalytic film on the air duct walls, the air passing through the air ducts will automatically get in contact with the photocatalyst, such that the photocatalytic reaction can take place once the luminaire is turned on. Due to the film shape, the photocatalytic material can be used in a particularly cost-effective manner.

The film with the photocatalytic material can be a coating film produced by spraying, brushing, dip-coating, and/or roller coating. These techniques are suitable for producing films in a wide range of thicknesses. In some embodiments, the photocatalyst is sprayed on one or more surfaces of the inner housing or diffusor and the outer housing, thus increasing the effective area of the photocatalyst. In some embodiments, only inner surfaces and no exterior surfaces are coated with the photocatalyst material, in order to protect the coating with the photocatalyst material.

The film of the photocatalytic material may be, in particular, a single-layer film of the photocatalytic material. The thickness of the film may be less than 0.1 mm, more specifically less than 0.05 mm.

In some embodiments, the film with the photocatalytic material comprises a protective coating layer and a photocatalytic material layer. The protective coating layer may comprise, in particular, crystalline-free silica and/or water. The photocatalytic layer may comprise, in particular, titanium dioxide, water, and/or crystalline-free silica. The thickness of such a film may range between 200 nm and 1,000 nm, more specifically between 300 nm and 600 nm.

The photocatalytic material may be a compound material comprising a matrix material or coating material and the photocatalyst material. The matrix material may comprise, in particular, polyurethane acrylic copolymer, silicon acrylic copolymer, silicone, and/or water.

By using the compound material with the matrix material and the photocatalyst material, the photocatalytic element can be easily formed on solid surfaces of the optical and/or mechanical components of the luminaire. The photocatalyst material may comprise tungsten trioxide, titanium dioxide, copper oxide, and/or water. These materials can serve as a photocatalyst under exposure to the visible light.

The light source may be an LED (light-emitting diode) light source generating a white light with a correlated color temperature in the range between 2,200K and 10,000K. Thus, the visible light generated by the light source may cover essentially the whole spectrum of CCT (correlated color temperature) white light spectrum between extremely warm light and extremely cold light.

In the following description, details are provided to describe the embodiments of the present specification. It shall be apparent to one skilled in the art, however, that the embodiments may be practiced without such details.

Some parts of the embodiments have similar parts. The similar parts may have the same names or similar part numbers. The description of one part applies by reference to another similar part, where appropriate, thereby reducing repetition of text without limiting the disclosure.

DETAILED DESCRIPTION

Figure 1:
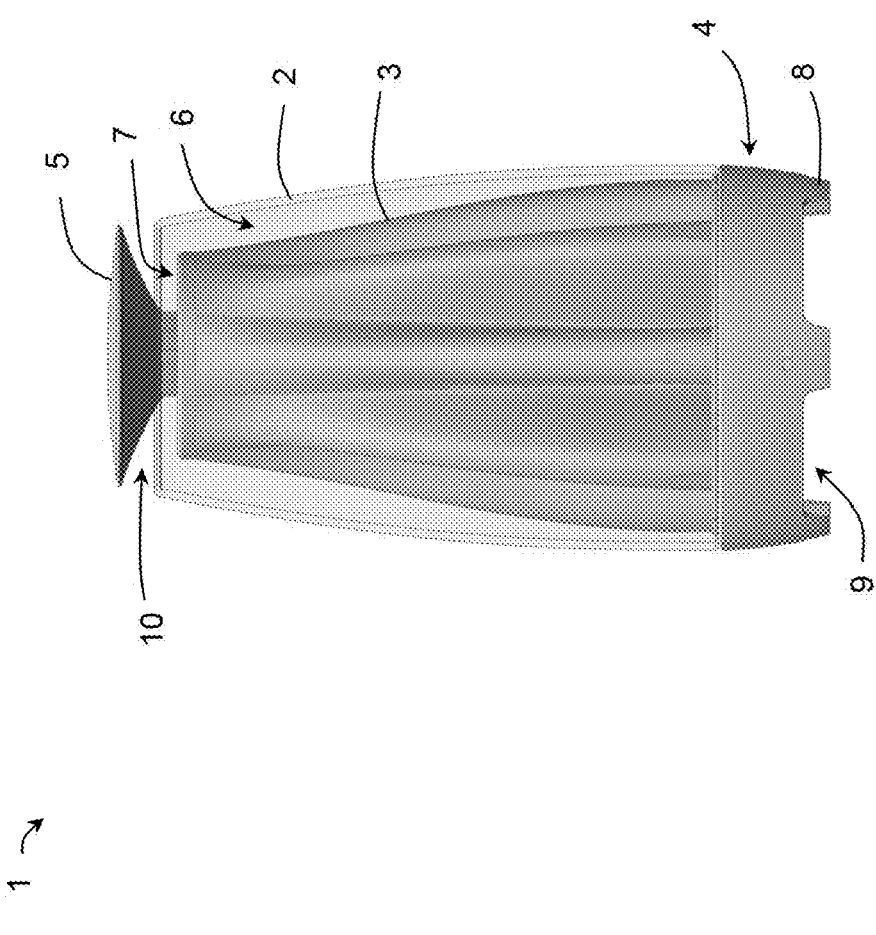
FIG. 1 shows a schematic side view of a luminaire according to an embodiment.

FIG. 1 shows a schematic side view of a luminaire 1 according to an embodiment. In the embodiments of FIG. 1, the luminaire 1 is configured as a tabletop luminaire or a standing lamp and comprises a light source for generating a visible light, as well as electrical circuitry for driving the light source. The light source and the electrical circuitry are not shown. The luminaire 1 comprises an outer housing 2, an inner housing 3, a base housing 4, and a top cap 5. The outer housing 2 is shown as a semitransparent cover, in order to better illustrate the inner structure of the luminaire 1. As it can be seen from FIG. 1, the inner housing 3 has a corrugated profile with a plurality of radially extending wings tapered towards the upper end of the luminaire 1.

In the embodiment of FIG. 1, the luminaire 1 comprises an outer duct 6 and an inner duct 7 extending between the base housing 4 and the top cap 5 of the luminaire 1.

The bottom housing 4 comprises standing feet 8 configured for positioning the luminaire 1 on a flat surface such that an air inlet 9 or air inlet gap between the flat surface and the base housing 4 remains. The top cap 5 is equipped with a closing mechanism (not shown) such that the top cap 5 can be closed or open. In the open state of the top cap 5, corresponding to FIG. 1, there remains an air outlet 10 as a gap between the outer housing 2 and the top cap 5, serving as an air outlet.

Figure 2:
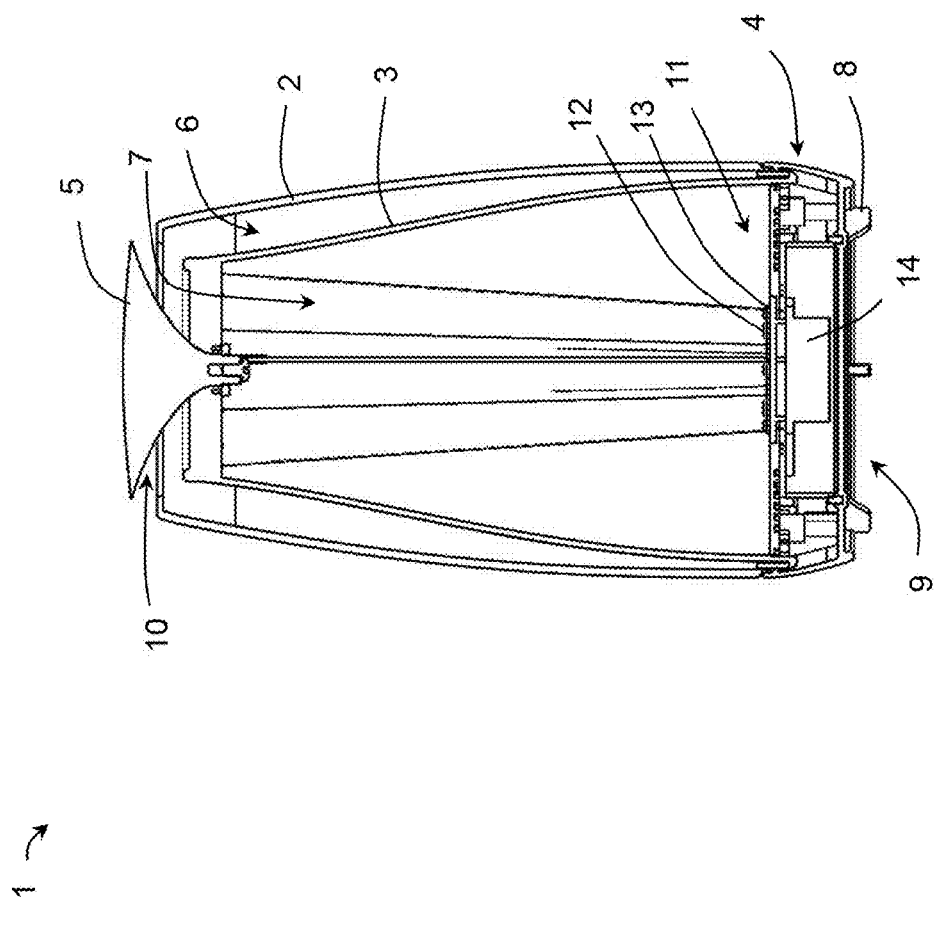
FIG. 2 shows a schematic cross-sectional view of the luminaire of FIG. 1.

FIG. 2 shows a schematic cross-sectional view of the luminaire 1 of FIG. 1. As it can be seen from FIG. 2, the light source 11 is arranged in the lower part of the luminaire 1. In this embodiment, the light source 11 is an LED light source or LED light engine comprising a number of LEDs 12 mounted on a PCB 13 (printed circuit board). The luminaire 1 further comprises a fan 14 arranged in the base housing 4, under the light source 11. The fan 14 is configured for forcing the air through the outer duct 6 and the inner duct 7 from the air inlet 9 to the air outlet 10.

Figure 3:
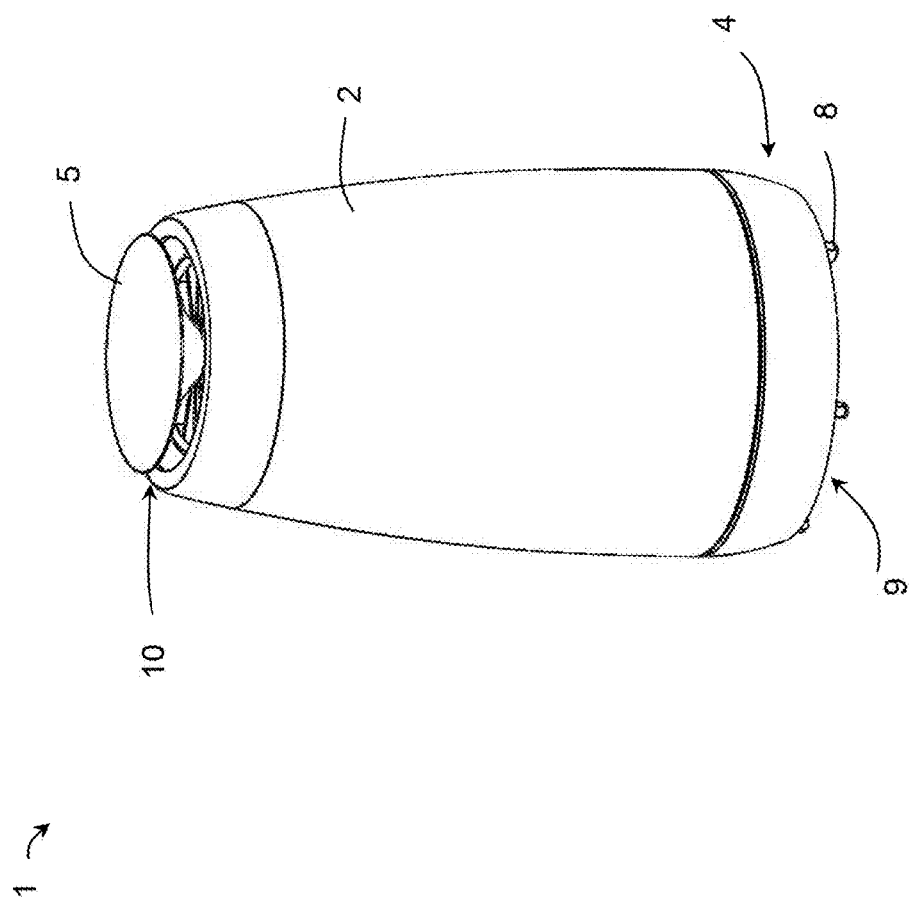
FIG. 3 shows a schematic perspective view of the luminaire of FIG. 1.

FIG. 3 shows a schematic perspective view of the luminaire 1 of FIG. 1. As can be seen from FIG. 3, the luminaire 1 has an essentially symmetrical shape of a rotational body with a vertical symmetry axis. The outer housing 2, the base housing 4, and the top cap 5 have a smoothly shaped outer surface.

Figure 4:
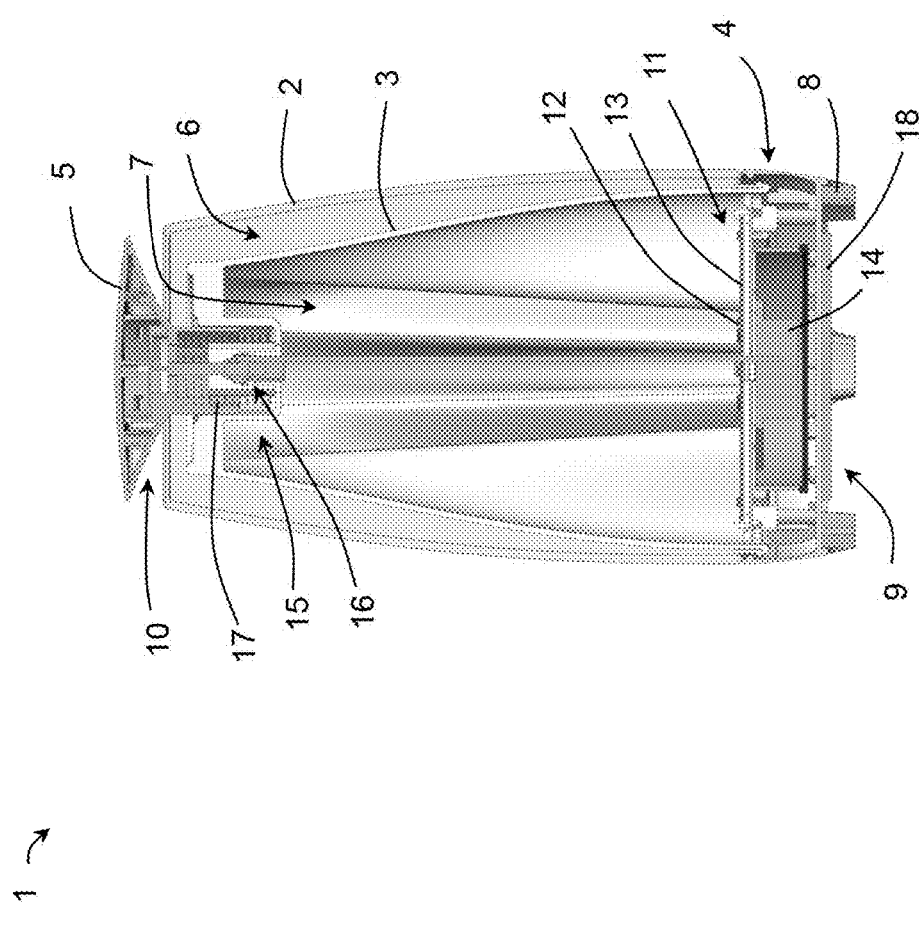
FIG. 4 shows a schematic cross-sectional view of the luminaire of FIG. 1.

FIG. 4 shows a schematic cross-sectional view of the luminaire 1 of FIG. 1. The cross-sectional view of FIG. 3 reveals some more details of the luminaire 1. In particular, it shows the closing mechanism 15 of the top cap 5. The closing mechanism 15 comprises a locking mechanism 16 and a spring 17, configured for closing and opening the top cap 5. The cross-sectional view of FIG. 4 also shows a dust filter 18 arranged at the bottom of the base housing 4.

Figure 5:
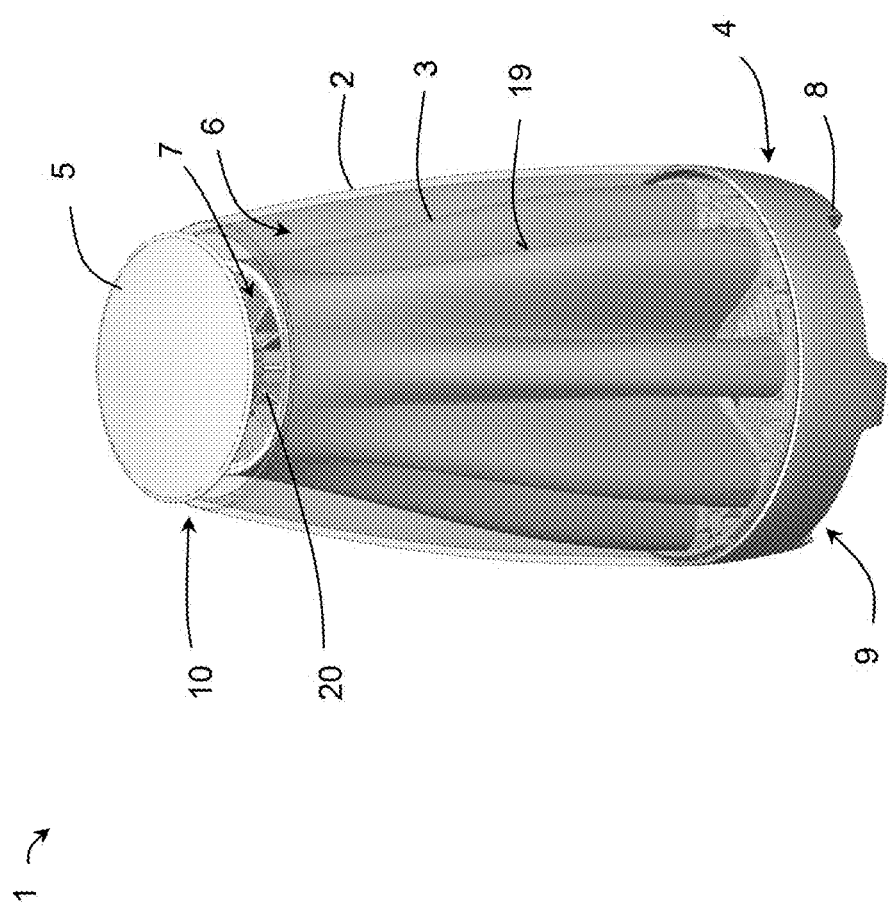
FIG. 5 shows a schematic perspective view of the luminaire of FIG. 1.

FIG. 5 shows a schematic perspective view of the luminaire 1 of FIG. 1. Similar to FIG. 1, the outer housing 2 is shown as a semitransparent cover, in order to better illustrate the inner structure of the luminaire 1. In the view of FIG. 5, one can see the corrugated shape of the inner housing 3 with radially extending wings 19 and a smoothly shaped outer surface 20. The cross section of the inner housing 3 in a horizontal plane smoothly changes from an essentially star-shaped configuration at the base housing 4 to an essentially circular configuration at the top cap 5 of the luminaire 1. FIG. 5 also shows vertical fins 21 which are radially arranged in the inner duct 7 close to its upper end. The fins 21 serve for holding the closing mechanism 15 in its position.

Figure 6:
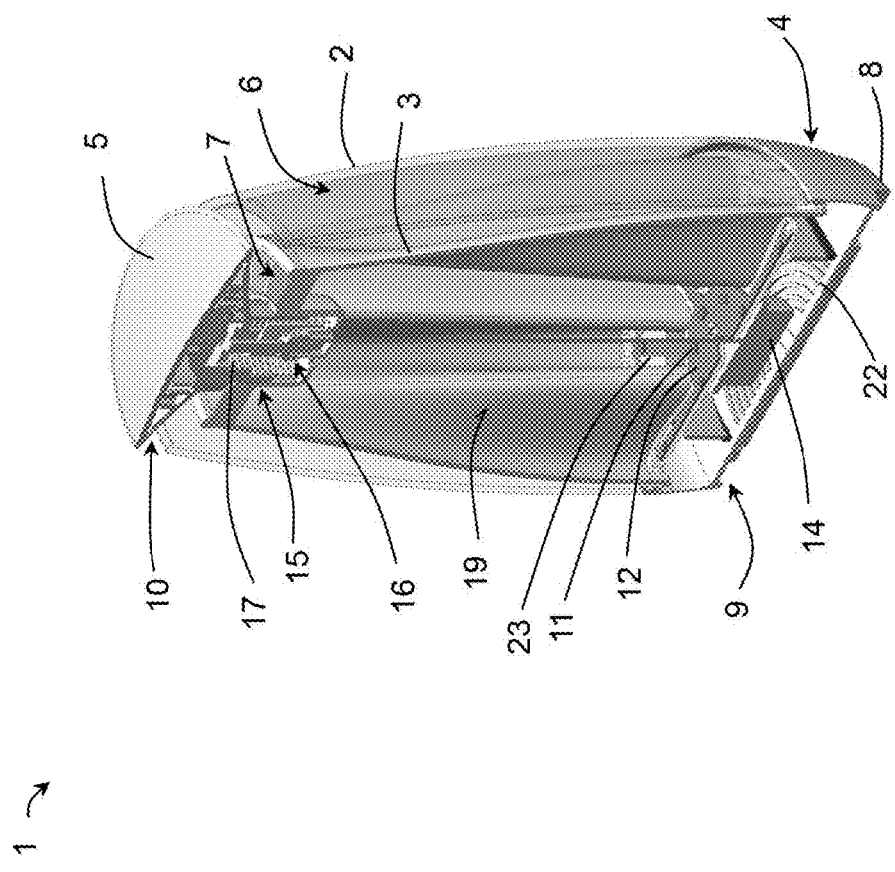
FIG. 6 shows a schematic cross-sectional perspective view of the luminaire of FIG. 1.

FIG. 6 shows a schematic cross-sectional perspective view of the luminaire 1 of FIG. 1. As it can be seen in FIG. 6, the PCB 13 is star-shaped as well, and the LEDs 12 mounted on the PCB 12 also build a star-shaped arrangement, such that the wings 19 of the inner housing 3 can be illuminated from inside by the LEDs 11 arranged beneath each wing 19 of the inner housing 3. An air inlet grid 22 is arranged in the bottom of the base housing 4 under the fan 8. Between an inner surface 23 of the inner housing 3 and the PCB 13, there is a gap 23 for air to flow into the inner duct 7.

Figure 7:
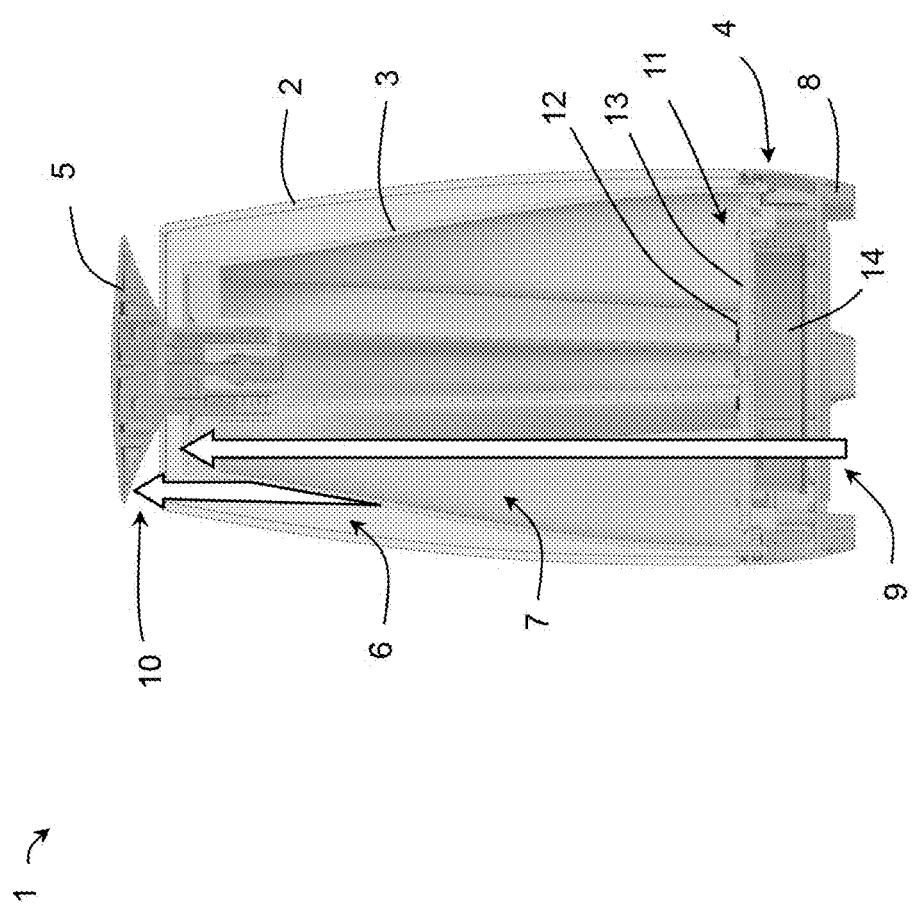
FIG. 7 shows a schematic cross-sectional view of the luminaire of FIG. 1.

FIG. 7 shows a schematic cross-sectional view of the luminaire 1 of FIG. 1 illustrating the air flow within the luminaire 1. In particular, FIG. 7 shows the cross-sectional view of FIG. 4 with additional vertical arrows extending form the base housing 4 to the top cap 5 of the luminaire 1 for illustrating the air flow. An inner arrow extending vertically from the air inlet 9 towards the air outlet 10 is arranged within the inner duct 7 and illustrates the air flow with the inner duct 7. An outer arrow extending vertically from the air inlet 9 towards the air outlet 10 is arranged within the outer duct 6 and illustrates the air flow within the outer duct 6.

Figure 8:
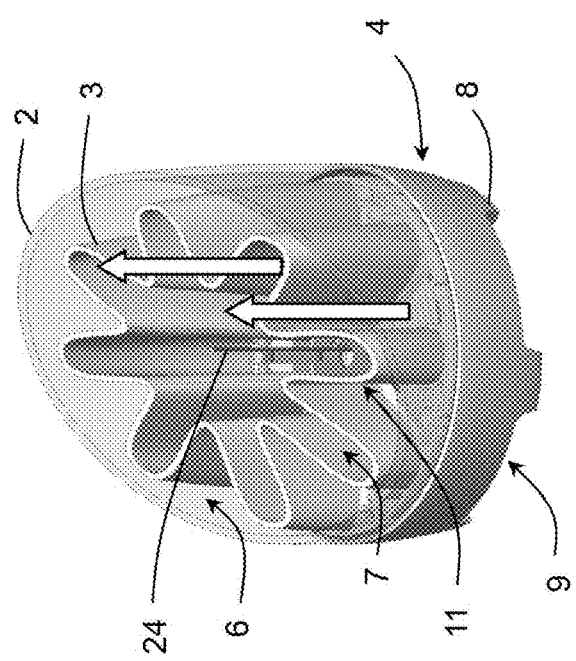
FIG. 8 shows an oblique cross-sectional view of the luminaire of FIG. 1.

FIG. 8 shows an oblique cross-sectional view of the luminaire 1 of FIG. 1. In the oblique cross section of FIG. 8, the air flow within the luminaire 1, illustrated by the arrows showing upwards, can be seen particularly well. Further, an electrical connection 24 extending vertically in the middle of the luminaire 1 for controlling the closing mechanism 15 can be seen as well.

Figure 9:
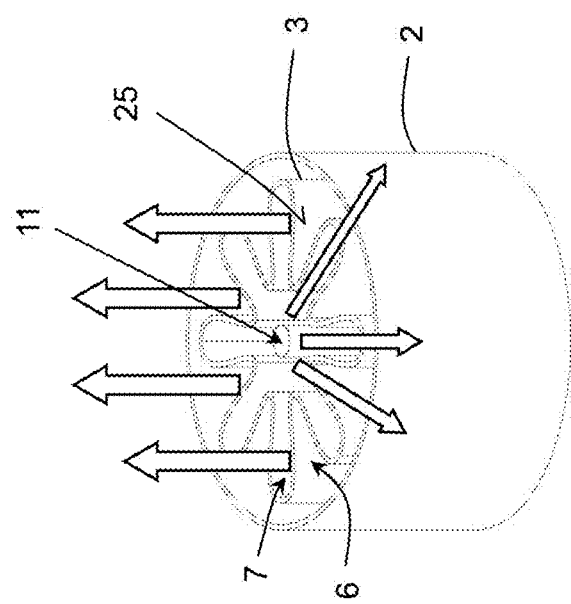
FIG. 9 illustrates the photo-catalyzation process in a luminaire according to an embodiment.

FIG. 9 illustrates the photo-catalyzation process in a luminaire 1 according to an embodiment. In this embodiment, the luminaire 1 essentially corresponds to the luminaire of FIG. 1, wherein the light source 11 is a linear light source extending vertically along the symmetry axis of the inner housing 3 and the outer housing 2. The inner housing 3 and the outer housing 2 comprise a diffusively scattering translucent walls with a photocatalyst material. The air flow along the inner duct 7 and the outer duct 6 is symbolized by the vertical arrows. The light propagation from the light source 11 through the wall of the inner housing 3 and the outer housing 2 is symbolized by arrows extending vertically. The photocatalyst material is applied as a coating 25 on the walls of the inner housing 3 and the outer housing 2. The light travelling from the light source 11 through the translucent walls of the inner housing 3 and the outer housing 2, symbolized by radial arrows, interacts with the photocatalyst material on the walls of the inner housing 3 and the outer housing 2 such that a photocatalytic reaction in the inner duct 7 and the outer duct 6 can take place.

Figure 10:
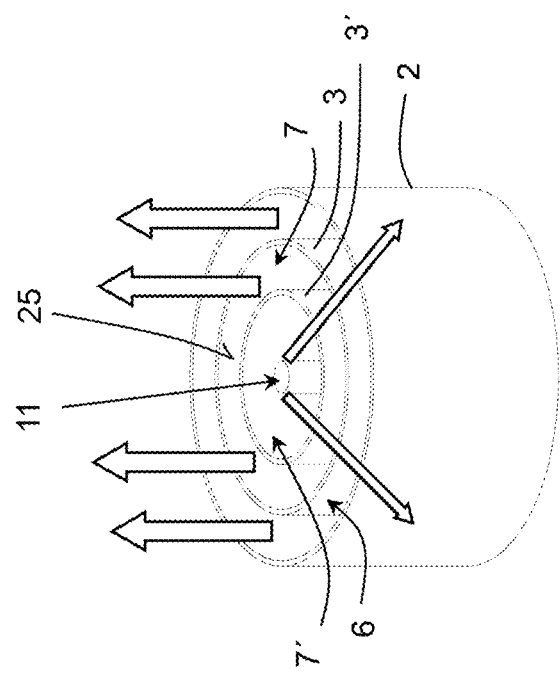
FIG. 10 illustrates the photo-catalyzation process in a luminaire according to another embodiment.

FIG. 10 illustrates the photo-catalyzation process in a luminaire 1 according to another embodiment. The embodiment of FIG. 10 essentially corresponds to the embodiment of FIG. 9, wherein the luminaire 1 comprises three coaxially arranged housings 2, 3, 3' building three coaxial ducts 6, 7, and 7'. The walls of the inner housings 3, 3' and the outer housing 2 are formed as translucent diffusers configured for diffusively scattering the light generated by the light source 11. The vertical arrows illustrate the air flow through the ducts 6, 7, and 7', and the radial arrows symbolize the light propagation from the light source 11 outwards through the walls of the coaxial housings 2, 3, and 3'.

In operation, the air is forced by the fan 14 into the luminaire 1 such that the air passes through the inner ducts 7, 7' formed within the inner housings 3, 3' and the outer duct 6, formed between the inner housing 3 and the outer housing 2 of the luminaire 1. Thus, the part of the air pressed into the luminaire 1 body by the fan 14 1 will reach the air outlet 10 at the top through the passage between the luminaire housing or outer housing 2 and the inner housing 3, and the other part of the compressed air will reach the air outlet 10 through the inner ducts 7, 7' formed inside the inner housing 3.

In some embodiments, the luminaire 1 may comprise a plurality of housings and a plurality of ducts, respectively. By increasing the number of ducts, the overall wall area exposed to the radiation and to the air can be increased, resulting in increased disinfection effect of the luminaire 1.

Figure 11:
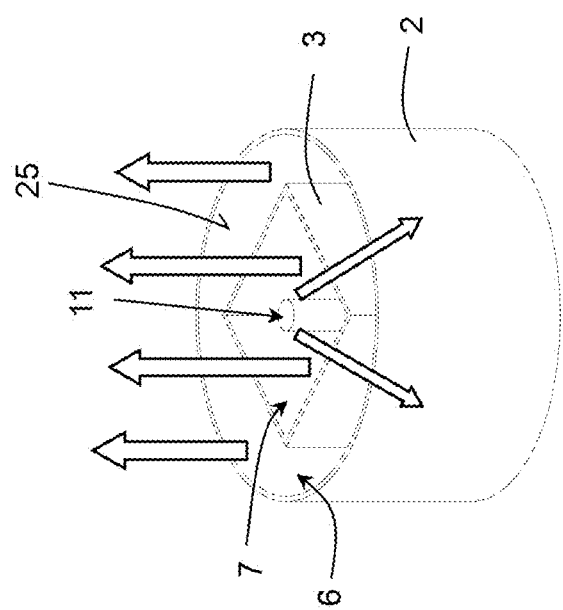
FIG. 11 illustrates the photo-catalyzation process in a luminaire according to still another embodiment.

FIG. 11 illustrates the photo-catalyzation process in a luminaire 1 according to still another embodiment. In this embodiment, the inner housing 3 has an essentially rectangular cross section, and the outer housing 2 an essentially circular cross section.

Figure 12:
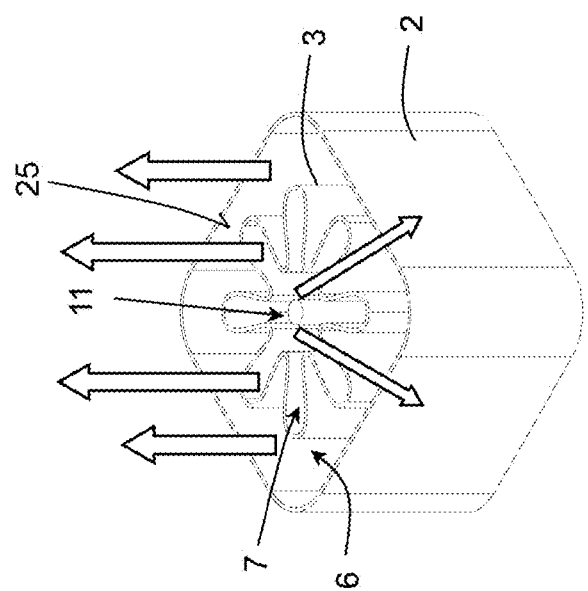
FIG. 12 illustrates the photo-catalyzation process in a luminaire according to another embodiment.

FIG. 12 illustrates the photo-catalyzation process in a luminaire 1 according to another embodiment. In this embodiment, the inner housing 3 has a corrugated shape, and the outer housing 2 has an essentially rectangular shape with smooth angles. The embodiments shown in FIGS. 9 to 12 illustrate, in particular, that the luminaire 1 may have different external design as well as a variety of possible housing configurations.

Figure 13:
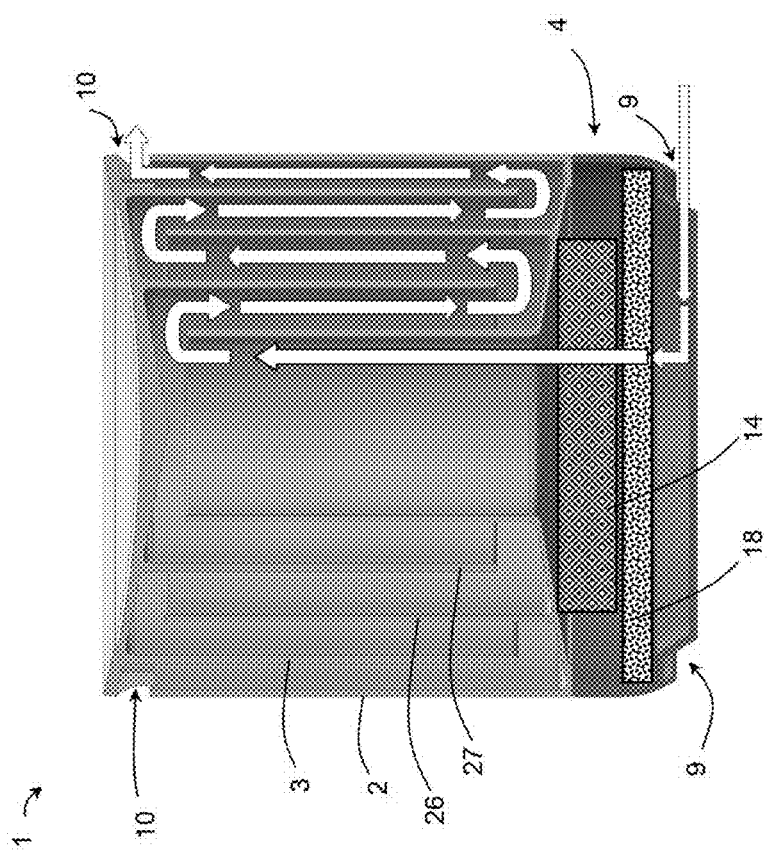
FIG. 13 shows a schematic cross-sectional view of a luminaire with a folded airway design.

FIG. 13 shows a schematical cross-sectional view of a luminaire 1 with a folded air way design. For the sake of simplicity, only the airflow system of the luminaire 1 is shown. The luminaire 1 comprises an outer housing 2 with a number of partitioning walls 26 extending upwards from the bottom of the outer housing 2. The luminaire 1 further comprises an inner housing 3 with a number of partitioning walls 27 extending downwards from the top of the inner housing 3. The outer housing 2 or the bottom housing and the inner housing 3 or top housing are inserted into each other in such a way that the partitioning walls 26 of the outer housing 2 and the partitioning walls 27 of the inner housing 3 form a folded way duct extending between the air inlet 9 or intake and the air outlet 10. The air flow system of the luminaire 1 further comprises a fan 14 and a dust filter 18 arranged in the region of the base housing 4 of the luminaire 1. Due to the folded airway design, overall wall area exposed to the radiation and to the air flow can be increased, resulting in an increased disinfecting effect of the luminaire 1.

The photocatalytic element may comprise a film at least partially covering at least one wall of the at least one air duct. By providing the photocatalytic film on the air duct walls, the air passing through the air ducts will automatically get in contact with the photocatalyst such that the photocatalytic reaction can take place once the luminaire 1 is turned on. Due to the film shape, the photocatalytic material can be used in a particularly cost-effective manner.

The photocatalytic film may be applied by spraying, brushing, dip-coating, or roller coating. The photocatalytic film may include one or more photocatalytic materials that can respond to visible light, in particular, both visible light and UV light.

In particular, the photocatalytic material may have a composition with one or several compounds and, in particular, may comprise a two-component mixture of the type A+B. Therein, the first component A is a photocatalytic material which may comprise tungsten trioxide, titanium dioxide, copper oxide, and/or water. The second component B is a coating material comprising polyurethane acrylic copolymer, silicon acrylic copolymer, silicone, and/or water. In some embodiments, the coating film comprises a single layer of the mixture. The coating film thickness may be less than 0.1 mm. In some embodiments, the coating film comprises a protective layer with crystalline-free silica and/or water and a photocatalytic layer with titanium dioxide, water, and/or crystalline-free silica. The overall film thickness of coating film may range from 200 nm to 1,000 nm.

The optical element 3 may be a diffuser, a lens, and/or a reflector. The photocatalytic element can be excited by the visible light generated by the luminaire 1 as well as by an external light (e.g., from the sun or other light source), so the sterilization can take place even if the luminaire 1 is off.

By applying such coating on the translucent walls of the ducts of the luminaire 1, a photocatalytic area or active area can be provided, in order to annihilate or destroy viruses and bacteria in its surroundings, leading to a healthier working and/or living environment. Thus, the present principles allow to combine lighting and sterilization, air cleaning by providing a compact photocatalyst multifunctional luminaire setting.

The photocatalytic coating may be a commercially available coating showing photocatalytic properties under visible light impact. There are several suppliers in the market (e.g., Raze Technology Limited, Shin-Etsu Chemical Co., Ltd., and others).

Thus, the multi-featured design of a luminaire, described above, combines two functions important for indoor residential applications, namely, a luminaire function and a photocatalyst air sanitizer function, in a single small-sized integrated product.

The luminaire further provides high efficiency for the photocatalyst coating to sanitize the surrounding air forced through the luminaire by an electrically powered fan to increase the air circulation of the product's surrounding space in small indoor residential settings.

Furthermore, a unique design of the equal bypass-ratio duct housings enables the maximum contact area with the air in order to perform the sanitization reaction. Besides, this integrated design also enables the luminaire to produce ample lighting output while performing sanitization through the photocatalyst. The multilayered luminaire structure can protect the photocatalyst coating from external wear and tear.

While at least one exemplary embodiment has been presented in the foregoing detailed description, it should be appreciated that a vast number of variations exists. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments.

REFERENCE SYMBOLS AND NUMERALS

1 luminaire
2 outer housing
3 inner housing
4 base housing
5 top cap
6 outer duct
7 inner duct
8 foot
9 air inlet
10 air outlet
11 light source
12 LED
13 PCB
14 fan
15 closing mechanism
16 locking mechanism
17 spring
18 dust filter
19 wing
20 outer surface
21 fin
22 air inlet grid
23 inner surface
24 electrical connection
25 coating
26 partitioning wall
27 partitioning wall

What is claimed is:
1. A luminaire comprising:
a light source configured for generating a light;
an electrical circuitry configured for driving the light source; and a first housing and a second housing disposed in a coaxially nested arrangement so as to define therebetween at least one air duct extending from an air inlet at a first end of the luminaire to an air outlet at an opposing second end of the luminaire, with air duct walls comprising a photocatalytic element, wherein:

the air duct walls are solid, non air permeable, and at least partially light-transmissive; and the at least one air duct is configured such that air flowing through the at least one air duct is able to get in contact with the photocatalytic element and participate in a photocatalytic reaction under exposure to at least one of:

the light generated by the light source; and an external light.

2. The luminaire according to claim 1, wherein:

the air duct walls of the at least one air duct are configured to at least partially serve as at least one of a lens, a diffuser, and a reflector; and the photocatalytic element is at least one of:
  formed as an integral part of the air duct walls; and
  arranged on the air duct walls.

3. The luminaire according to claim 1, wherein the at least one air duct comprises at least two air ducts with an essentially equal bypass-ratio.

4. The luminaire according to claim 1, wherein the first housing and the second housing each comprise a number of partitioning walls which are configured such that, when the first housing and the second housing are arranged together, the partitioning walls of the first housing and the partitioning walls of the second housing form a folded airway with a number of air ducts extending from the air inlet to the air outlet.

5. The luminaire according to claim 1, further comprising a fan configured for forcing air through the at least one air duct.

6. The luminaire according to claim 1, wherein the photocatalytic element comprises a photocatalytic film at least partially covering at least one wall of the at least one air duct and having an absorption spectrum in the range of 380-780 nm.

7. The luminaire according to claim 6, wherein the photocatalytic film is a single-layer film comprising a photocatalytic material.

8. The luminaire according to claim 6, wherein the photocatalytic film is a multi-layer film comprising:
  a protective coating layer; and
  a photocatalytic material layer.

9. The luminaire according to claim 6, wherein the photocatalytic film comprises a compound material comprising:
  a matrix material comprising at least one of polyurethane acrylic copolymer, silicon acrylic copolymer, silicone, and water; and
  a photocatalyst material comprising at least one of tungsten trioxide, titanium dioxide, copper oxide, and water.

10. The luminaire according to claim 1, wherein:
  the light source is a light-emitting diode (LED) light source; and
  the light generated by the light source is a white light with a correlated color temperature (CCT) in the range of 2,200-10,000 K.

11. The luminaire according to claim 1, further comprising:
  a base disposed at the first end of the luminaire; and
  a cap disposed at the second end of the luminaire.

12. The luminaire according to claim 11, wherein the first housing and the second housing are substantially tubular in shape, providing a first hole at the first end of the luminaire and a second hole at the second end of the luminaire.

13. The luminaire according to claim 12, wherein the cap comprises a closing mechanism configured to open and close the cap in relation to the second end.

14. The luminaire according to claim 13, wherein:
  the luminaire further comprises a plurality of vertical fins radially arranged in the at least one air duct; and
  the cap is configured to interface with the plurality of vertical fins.

15. The luminaire according to claim 13, wherein:
  when the closing mechanism is in a closed position, the cap substantially fills or covers the second hole; and
  when the closing mechanism is in an open position, a gap exists between the cap and the second hole.

16. The luminaire according to claim 13, wherein the closing mechanism is electronically controlled.

17. The luminaire according to claim 1, wherein at least one of the first housing and the second housing has a corrugated profile with a plurality of radially extending wings.

18. The luminaire according to claim 17, wherein at least one of the plurality of radially extending wings tapers in profile along a longitudinal extent thereof.

19. The luminaire according to claim 18, wherein a cross section of at least one of the first housing and the second housing, as taken along a horizontal plane, transitions from a substantially star-shaped configuration at the first end to a substantially circular configuration at the second end.

* * * * *